United States Patent
Gabriel et al.

(10) Patent No.: US 10,975,097 B2
(45) Date of Patent: Apr. 13, 2021

(54) PROCESS TO CONVERT TECHNICAL ASCOMYCIN INTO PURIFIED PIMECROLIMUS

(71) Applicants: Meda Pharma GmbH & Co. KG, Homburg (DE); Meda AB, Solna (SE)

(72) Inventors: Borut Gabriel, Borovnica (SI); Aljaž Kajtna, Ljubljana (SI); Ajna Lukic, Smarje-Sap (SI); Dominic De Souza, Regau (AT); Werner Hasselwander, Oberkirch (DE)

(73) Assignee: Meda AB

( * ) Notice: Subject to any disclaimer, the term of this patent is extended or adjusted under 35 U.S.C. 154(b) by 0 days.

(21) Appl. No.: 16/610,098

(22) PCT Filed: May 2, 2018

(86) PCT No.: PCT/EP2018/061235
§ 371 (c)(1),
(2) Date: Nov. 1, 2019

(87) PCT Pub. No.: WO2018/202733
PCT Pub. Date: Nov. 8, 2018

(65) Prior Publication Data
US 2020/0079792 A1    Mar. 12, 2020

Related U.S. Application Data

(60) Provisional application No. 62/492,394, filed on May 1, 2017.

(51) Int. Cl.
*C07D 498/18* (2006.01)

(52) U.S. Cl.
CPC ........ *C07D 498/18* (2013.01); *C07B 2200/13* (2013.01)

(58) Field of Classification Search
CPC .................................................. C07D 498/18
See application file for complete search history.

(56) References Cited

U.S. PATENT DOCUMENTS

| 4,737,292 A | 4/1988 | Ritacco et al. |
| 10,760,070 B2 | 9/2020 | Funkner et al. |

FOREIGN PATENT DOCUMENTS

| WO | WO 2001/090110 | 11/2001 |
| WO | WO 2006/040111 | 4/2006 |
| WO | WO 2006/060614 | 6/2006 |
| WO | WO 2010/134027 | 11/2010 |

OTHER PUBLICATIONS

International Preliminary Report on Patentability for PCT/EP2018/061235, dated Nov. 6, 2019.
International Search Report from PCT/EP2018/061235, dated Jun. 14, 2018.

*Primary Examiner* — Bruck Kifle

(57) ABSTRACT

The present disclosure is directed to an improved process to convert crude ascomycin to purified pimecrolimus. Crude ascomycin is chlorinated with triphenylphosphine and N-chlorosuccinimide (NCS) to yield crude pimecrolimus, which is then purified further by HPLC and subsequent crystallization. The processes of the present disclosure enable the removal of close homologs of pimecrolimus by high-pressure liquid chromatography without prior purification of the ascomycin starting material. This improvement may make the conversion of ascomycin to pimecrolimus industrially applicable and less expensive.

27 Claims, 2 Drawing Sheets

PROCESS TO CONVERT TECHNICAL ASCOMYCIN INTO PURIFIED PIMECROLIMUS

CROSS REFERENCE TO RELATED APPLICATIONS

This application is a national phase application under 35 U.S.C. § 371 of International Application No. PCT/EP2018/061235, filed on May 2, 2018, which claims priority to U.S. Provisional Patent Application No. 62/492,394 filed May 1, 2017. The contents of each of the above-identified applications is hereby fully incorporated herein by reference.

TECHNICAL FIELD

The present disclosure describes a process for the production of 33-epi-chloro-33-desoxyascomycin, also known as pimecrolimus (formula I):

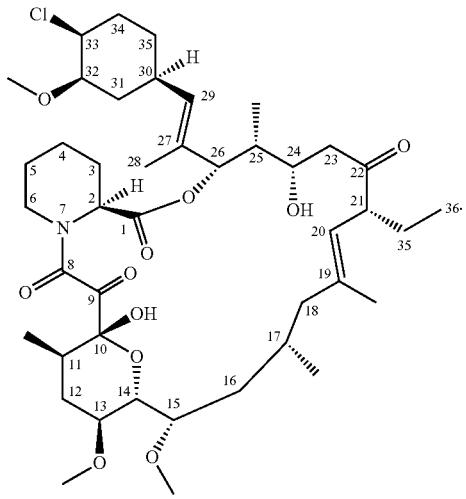

(I)

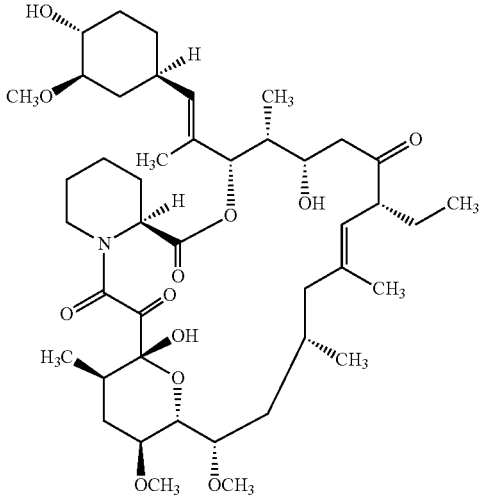

ASC

BACKGROUND

Pimecrolimus (formula I) is a known macrolide compound, disclosed in EP 0427680, having anti-inflammatory, anti-proliferative and immunosuppressive properties. Pimecrolimus is useful for the treatment of immunological-mediated diseases, e.g. treatment and prevention of inflammatory, auto-immune and hyperproliferative diseases, e.g. including skin diseases, such as psoriasis, atopic dermatitis; immune-mediated conditions of the eye, such as auto-immune diseases, e.g. including uveitis, keratoplasty and chronic keratitis; allergic conditions, e.g. vernal conjunctivitis, inflammatory conditions, corneal transplants. It is approved as the active pharmaceutical ingredient in Elidel® for topical treatment of atopic dermatitis.

Several different procedures, using different process steps, with or without protection groups, are known to produce 33-epichloro-33-desoxyascomycin.

EP 0427680 describes the synthesis of pimecrolimus from ascomycin (formula ASC) in 4 chemical steps with 3 different silylated compounds as intermediates. The overall yield is 16%.

WO2010/134027A describes the synthesis of pimecrolimus from ascomycin in 5 chemical and enzymatic steps with 4 different compounds as intermediates using reagents and enzymes like vinyl acetate, Novozym 435, tert.-butyldimethylsilyl triflourmethanesulfonate, 2,6-lutidine, dichlorotriphenylphosphorane, etc. The overall yield is 30.8%. The synthesis through ascomycin diacetate needs 4 chemical and enzymatic steps and involves 3 intermediates and cancerogenic and toxic reagents such as carbontetrachloride and dimethylaminopyridine. The overall yield of about 13.9% of theory is poor.

WO2006/060614 describes a method to convert ascomycin into pimecrolimus without protecting the C24 hydroxy group but converting the C32 Hydroxy group into the leaving group trifluoromethanesulfonate. A HPLC purity of 95.75 area % is achieved.

US2009/0082386 describes a method to purify ascomycin and to convert such purified ascomycin into pimecrolimus. Ascomycin is purified first by column chromatography and is then subjected to multiple crystallizations in order to purify the starting material, from which pimecrolimus is formed. The overall yield calculated from this process is 17.6% of theory.

WO2005/010015 describes a method of purifying macrolides using sorption resins. From the elution rate and number of fractions it can be calculated that such purification is very time consuming and therefore not industrially applicable.

In WO2006/040111 the synthesis of pimecrolimus by chlorination of ascomycin with triphenylphosphine and N-chlorosuccinimide (NCS) is described. The mixture is worked up by extraction and chromatography on silica gel followed by crystallization from ethanol and water to give pimecrolimus with a purity of 98%. The yield is unsatisfactory since the raw material ascomycin is very valuable. In fact, high purity ascomycin must be used, which can be obtained only by complex countercurrent extraction as described in CH 692 839, U.S. Pat. Nos. 6,620,325 and 7,148,346. If commercially available, inexpensive technical-grade ascomycin is used, the resulting pimecrolimus contains ethyl and desmethylene homologues from the technical grade ascomycin and other related substances. Such technical grade pimecrolimus cannot be used as pharmaceutical ingredient.

Moreover, a purity of 98% for a pharmaceutically active substance such as pimecrolimus is not state of the art. More usual is a purity of 99% or more. Such high purity cannot be achieved with only chromatographic purification on silica gel as described in WO2006/040111. To achieve a purity of 99%, the crude pimecrolimus has to be processed by an elaborate countercurrent extraction as described in U.S. Pat. No. 7,148,346 followed by chromatographic purification and crystallization, causing further yield losses and additional manufacturing costs. As such, there remains a need in the art for methods of preparing purified pimecrolimus from crude or technical-grade ascomycin, without prior extensive purification of the crude or technical-grade ascomycin, that generates purified pimecrolimus.

SUMMARY

The following presents a simplified summary of one or more aspects of the present disclosure in order to provide a basic understanding of such aspects. This summary is not an extensive overview of all contemplated aspects and is intended to neither identify key or critical elements of all aspects nor delineate the scope of any or all aspects. Its purpose is to present some concepts of one or more aspects in a simplified form as a prelude to the more detailed description that is presented later.

In one embodiment, the present disclosure is directed to a process for preparing purified pimecrolimus, comprising:
 a) chlorinating crude ascomycin to provide crude pimecrolimus; and
 b) purifying the crude pimecrolimus by high-pressure liquid chromatography to provide purified pimecrolimus.

In a further aspect, said chlorinating step includes chlorinating the crude ascomycin with dichlorotriphenylphosphorane in an organic solvent. In a yet further aspect, the chlorinating step includes generating a chlorinating agent in situ from reaction of triphenylphosphine with a chlorinated alkane or N-chlorosuccinimide. In a further aspect, the chlorinating agent is dichlorotriphenylphosphorane.

In another aspect, the crude ascomycin used in the process contains not less than 90% ascomycin. In another aspect, the crude ascomycin used in the process contains up to 2% (w/w) 21-desmethylene ascomycin, up to 1.5% (w/w) 17-ethylascomycin, and/or up to 4% (w/w) 21-epi-ascomycin and 11-ethylascomycin. In one aspect, the crude ascomycin is a technical-grade ascomycin. In an aspect, the crude ascomycin is not purified prior to the chlorinating step.

In another aspect, the purified pimecrolimus contains a reduced concentration of the C21 epimer of pimecrolimus or one or more of the homologues of pimecrolimus, which differ only by 1 methylene group present at position C19, C17, C11 or absent at position C21, relative to the crude pimecrolimus.

In one aspect of the process, purifying the crude pimecrolimus via high-pressure liquid chromatography generates a target fraction containing pimecrolimus, and further comprising the step of crystallizing the pimecrolimus in said target fraction to provide purified pimecrolimus. In a further aspect, purifying the crude pimecrolimus via high-pressure liquid chromatography includes the following steps:
 i) purifying crude pimecrolimus via high-pressure liquid chromatography to give a main fraction, wherein said main fraction contains pimecrolimus;
 ii) concentrating and then diluting the main fraction;
 iii) recirculating the main fraction through high-pressure liquid chromatography; and
 iv) optionally repeating steps ii) and iii),
to generate the target fraction containing pimecrolimus. In a further aspect, the purified pimecrolimus is not subjected to further purification steps.

In one aspect of the invention, the high-pressure liquid chromatography uses a stationary phase selected from the group consisting of an alkylated silica, a diol silica, or a cyano silica. In another aspect, the high-pressure liquid chromatography uses a mobile phase selected from the group consisting of:
 a nonpolar solvent, polar protic solvent, and optional polar aprotic solvent;
 one or more $C_5$-$C_8$ alkanes, an ether, and isopropanol;
 one or more $C_5$-$C_8$ cycloalkanes, an ether, and isopropanol;
 one or more $C_5$-$C_8$ alkanes, an ether, and ethanol;
 one or more $C_5$-$C_8$ cycloalkanes, an ether, and ethanol;
 heptane 81.1±0.5%:methyl-tert.-butylether 14.4±0.5%: isopropanol 4.5 (4.2-4.9) %;
 $C_1$-$C_3$ alcohols or acetonitrile, optionally an ether, and optionally an acid; or water, a water miscible solvent, optionally an ether, and optionally an acid.

In another aspect, the purifying step involves purifying the crude pimecrolimus by high-pressure liquid chromatography over an octadecyl silica stationary phase with a 30% water:70% methanol mobile phase.

In one aspect of the invention, the process generates purified pimecrolimus that is is more than 98% pure, more preferably more than 99% pure, and still more preferably more than 99.5% pure.

Another embodiment of the invention includes a process for preparing purified pimecrolimus, which includes the steps of:
 a) purifying a crude pimecrolimus via high pressure liquid chromatography to generate a target fraction containing pimecrolimus, wherein said crude pimecrolimus is prepared by chlorination of crude ascomycin without further purification of the crude ascomycin;
 b) crystallizing the pimecrolimus in the target fraction to give purified pimecrolimus.

In a further aspect, the purified pimecrolimus is more than 98% pure, preferably more than 99% pure, and still more preferably more than 99.5% pure.

In another aspect, the crude ascomycin used in the process contains not less than 90% ascomycin. In yet another aspect, the crude ascomycin contains up to 2% (w/w) 21-desmethylene ascomycin, up to 1.5% (w/w) 17-ethylascomycin, and/or up to 4% (w/w) 21-epi-ascomycin and 11-ethylascomycin. The crude ascomycin may be a technical-grade ascomycin.

In yet another embodiment, the invention includes a process for preparing purified pimecrolimus, consisting of the following steps:
 a) chlorinating crude ascomycin to give crude pimecrolimus;
 b) purifying the crude pimecrolimus via high pressure liquid chromatography to generate a target fraction containing pimecrolimus; and
 c) crystallizing the pimecrolimus in the target fraction to give purified pimecrolimus.

In a further aspect of this invention, the purifying step b) includes the following purification steps:
 i) purifying crude pimecrolimus via high-pressure liquid chromatography to give a main fraction, wherein said main fraction contains pimecrolimus;

ii) concentrating and then diluting the main fraction;
iii) recirculating the main fraction through high-pressure liquid chromatography; and
iv) optionally repeating steps ii) and iii), to generate the target fraction containing pimecrolimus.

In yet another embodiment of the invention, the invention includes a process for preaparing purified pimecrolimus, consisting essentially of the following steps:

a) chlorinating crude ascomycin to give crude pimecrolimus;
b) purifying the crude pimecrolimus via high pressure liquid chromatography to generate a target fraction containing pimecrolimus; and
c) crystallizing the pimecrolimus in the target fraction to give purified pimecrolimus.

These and other aspects of the invention will become more fully understood upon a review of the detailed description, which follows.

DETAILED DESCRIPTION

Figure 1:
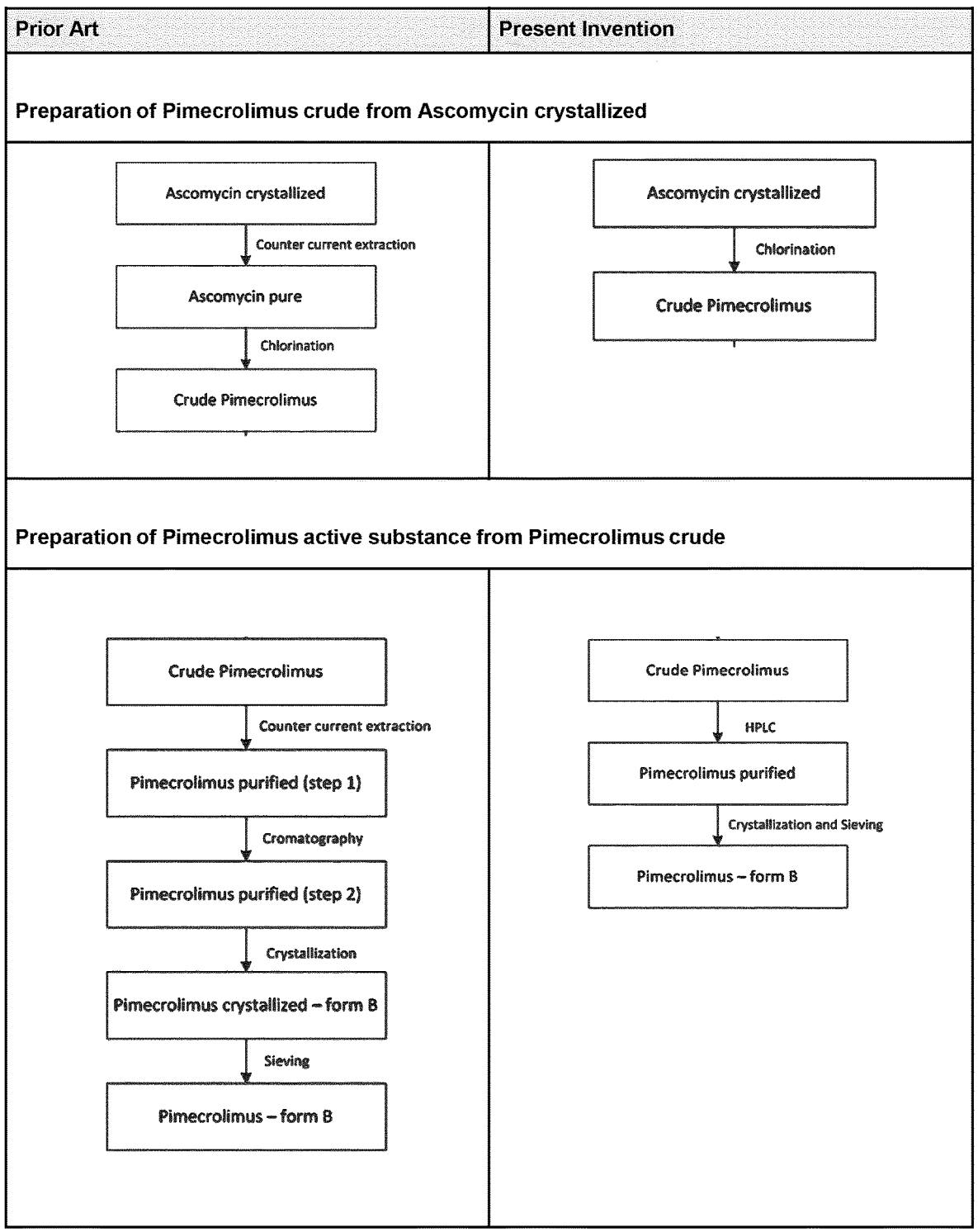
FIG. 1 shows a flow chart comparison of art-based methods of preparing pimecrolimus to the methods of the present disclosure.

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well known components are shown in block diagram form in order to avoid obscuring such concepts.

As used herein, the term "about" is defined to being close to as understood by one of ordinary skill in the art. In one non-limiting embodiment, the term "about" is defined to be within 10%, preferably within 5%, more preferably within 1%, and most preferably within 0.5%.

As used herein, "crude ascomycin" is defined as ascomycin containing more than about 0.2% (w/w) 21-desmethylene ascomycin, more than about 0.1% (w/w) 17-ethylascomycin, more than about 0.1% (w/w) 21-epi-ascomycin and 11-ethylascomycin and not more than 96% (w/w) ascomycin when measured by appropriate assay techniques (e.g., HPLC).

As used herein, "technical-grade ascomycin" is defined as crude ascomycin containing not less than 90% ascomycin when measured by appropriate assay techniques (e.g., HPLC). The technical-grade ascomycin may contain up to 2% (w/w) 21-desmethylene ascomycin, up to 1.5% (w/w) 17-ethylascomycin, and up to 4% (w/w) 21-epi-ascomycin and 11-ethylascomycin.

As used herein, "pure ascomycin" is defined as ascomycin containing less than 0.2% (w/w) 21-desmethylene ascomycin, 0.1% (w/w) 17-ethylascomycin, 0.1% (w/w) 21-epi-ascomycin and 11-ethylascomycin and not less than 96% (w/w) ascomycin when measured by appropriate assay techniques.

As used herein, "purified pimecrolimus" is defined as pimecrolimus that has been purified to effect removal of some or all impurities, including but not limited to the C21 epimer of pimecrolimus and homologues of pimecrolimus which differ only by 1 methylene group present at position C19, C17, C11 or absent at position C21.

As used herein, "substantially pure pimecrolimus" is pimecrolimus that is more than 98% pure, when measured by appropriate assay techniques.

As used herein, "room temperature" means about 25° C.

Although there are various procedures for the production or purification of pimecrolimus disclosed in the related art, there is still need for a process for production of purified pimecrolimus which is easy, provides good yield, inexpensive and industrially applicable. The invention herein lies in the ability to prepare purified pimecrolimus from a crude ascomycin (which may be a technical-grade ascomycin), while also reducing the number of steps needed to purify pimecrolimus. This results in a high-quality, less-expensive and more pure pimecrolimus active ingredient.

It has been surprisingly discovered that purified pimecrolmus can be prepared from crude ascomycin by chlorinating crude ascomycin and then purifying the resulting crude pimecrolimus with high pressure liquid chromatography. Thus, in one aspect of the invention includes a process for preparing purified pimecrolimus by purifying a crude pimecrolimus via high pressure liquid chromatography, wherein said crude pimecrolimus is prepared by chlorination of crude ascomycin without further purification of the crude ascomycin. In some embodiments, the crude ascomycin is technical-grade ascomycin. In some embodiments, the substantially pure pimecrolimus resulting from high-pressure liquid chromatography may be further crystallized in a crystallization step.

It was surprisingly discovered that the C21 epimer and the homologues of pimecrolimus, which differ only by 1 methylene group present at position C19, C17, C11 or absent at position C21, could be eliminated by HPLC. Up until now, the only possibility to eliminate these homologues from a mixture containing pimecroliums was to synthesize pimecrolimus from ascomycin that had been subjected to extensive purification steps. Therefore, the present application provides a simple process for the production of pure pimecrolimus from crude ascomycin without prior purification of ascomycin.

In the first step unprotected technical-grade ascomycin is reacted with an appropriate chlorinating agent, for example dichlorotriphenylphosphorane in an organic solvent, optionally in the presence of a base. The chlorinating agent and optionally the base, optionally each in organic solvent, or as such, are mixed and the mixture obtained is stirred at appropriate temperature for a reaction time sufficient for reaction.

In one embodiment, the chlorinating agent is dichlorotriphenylphosphorane. The chlorinating agent may be used as such or may be provided in situ, e.g. by treating triphenylphosphine with a chlorinated alkane, e.g. $C_1$-$C_2$ alkane, such as $CCl_4$, $C_2Cl_6$, preferably $CCl_4$; or by addition of triphenylphosphine to NCS in an organic solvent or mixtures of organic solvents.

In some embodiments, the organic solvents or mixtures of organic solvents may include hydrocarbons, e.g. aromatic hydrocarbons, e.g. benzene, toluene; ethers, such as tetrahydrofuran (THF); nitriles, e.g. acetonitrile; chlorinated alkanes, such as $CCl_4$; and mixtures of the foregoing solvents. In a further embodiment, the reaction mixture may be diluted with an appropriate additional solvent or solvents, which in some embodiments may be used to facilitate stirring.

In one embodiment, the organic solvent is selected from a group consisting of aromatic hydrocarbons (e.g., toluene), ethers (e.g., tetrahydrofuran), nitriles (e.g., acetonitrile), or halogenated alkanes (e.g., chlorinated alkanes), or mixtures thereof (e.g., toluene and acetonitrile). Preferable organic solvents include a chlorinated alkane, in case of using triphenylphosphine and a halogenated alkane for the preparation of dichlorotriphenylphosphorane as a chlorinating agent.

In case of using triphenylphosphine and a chlorinated alkane as a solvent, the chlorinated alkane may be used, in one aspect, as a halogen source for the production of dichlorotriphenylphosphorane and, in another aspect, as organic solvent, although the addition of further organic solvent, e.g. such as cited above, is not excluded. Especially preferred for the chlorination of ascomycin is the use of triphenylphosphine and NCS in tetrahydrofuran.

Suitable bases are organic bases known to persons of ordinary skill in the art, including but not limited to, e.g. nitrogen containing bases, such as tertiary amines or heterocyclic bases containing at least one nitrogen atom, more preferably aromatic heterocyclic bases, such as a pyridine or an imidazole; most preferably 2,4,6-trimethylpyridine (s-collidine).

The ratio of ascomycin and chlorinating agent is suitably at least an equivalent ratio (i.e., at least 1:1 of ascomycin: chlorinating agent), and preferably an excess of the chlorinating agent is used. The ratio of ascomycin to chlorinating agent is suitably about 1:1 to about 1:5. For example, ascomycin and the chlorinating agent are suitably used in a ratio from about 1:1 to about 1:3 (i.e., per equivalent of ascomycin, 1 to 3 equivalents of the chlorinating agent), such as from about 1:1 to about 1:2; e.g. from about 1:1 to about 1:5, preferably from about 1:1 to about 1:1.3, e.g. a ratio from 1:1 to 1:3, such as from 1:1 to 1:2; e.g. from 1:1 to 1:5, preferably from 1:1 to 1:1.3 may be appropriate.

The preferred initial molar excess of NCS to ascomycin is 0-30 Mol %. More preferably, the molar excess of NCS to ascomycin is 8 Mol %.

The ratio of ascomycin and the base should be at least an equivalent ratio (i.e., at least 1:1), and preferably an excess of the base is used. For example, the ascomycin and the base may be used in a ratio from about 1:1 to about 1:10 (per equivalent ascomycin, 1 to 10 equivalents of the base), such as from about 1:2 to about 1:10, e.g. from about 1:3 to about 1:9, preferably from about 1:2 to about 1:4, or any integer ratio or subrange in between.

The preferred initial molar excess of triphenylphosphine to ascomycin is 0-30 Mol %. More preferably, the initial molar excess of triphenylphosphine to ascomycin is 3 Mol %.

In case of using triphenylphosphine and a chlorinated alkane as a solvent, the chlorinated alkane may be used in one aspect as a halogen source for the production of dichlorotriphenylphosphorane and, in another aspect, as organic solvent, although the addition of further organic solvent, e.g. such as cited above, is not excluded.

Appropriate reaction temperatures include temperatures from room temperature to about 100° C., such as from room temperature to about 90° C., from room temperature to about 80° C., or from room temperature to about 70° C.

In case of using a chlorinated alkane, such as $CCl_4$, and triphenylphosphine for the production of the chlorinating agent, the preferable reaction temperature is the reflux temperature of the chlorinated alkane.

In case of using triphenylphosphine and NCS, suitable reaction temperatures include temperatures from room temperature to about 100° C. Preferred reaction temperatures are between 25 and 40° C. Suitable reaction times sufficient for reaction are between 1 and 40 hours. Preferably, the reaction time is between 10 and 20 hours. The required reaction time depends on the chosen temperature, and optimization of reaction time is within the knowledge of those of ordinary skill in the art. Reaction progress may be monitored using methods known to those of ordinary skill in the art, including, but not limited to, thin-layer chromatography, HPLC, and LC, each coupled with UV detection. Suitable wavelengths for UV detection for reaction monitoring can be determined by those of ordinary skill in the art and include, but are not limited to, 254 nm.

After sufficient reaction time, the reaction product is worked up, preferably by dilution with a water-immiscible solvent, such as cyclohexane, and reaction with an aqueous acid solution, such as citric acid. At least ⅓ mole of citric acid per mol of base (e.g. s-collidine) is used, preferably ⅓ to 1 mol, more preferably ⅔ mol. The aqueous acid solution may contain a water-miscible solvent, such as methanol or ethanol, preferably methanol. The aqueous and water-immiscible layers are separated. The water-immiscible layer may be extracted with water and optionally methanol again.

After extraction the solvent is evaporated from the organic phase, using methods known to persons of ordinary skill in the art to give a residue. The residue is then dissolved in a suitable solvent. Suitable solvents are solvents in which pimecrolimus is readily soluble and which can be removed easily by evaporation, such as acetone, acetonitrile, ethylacetate, methanol, ethanol, isopropanol, preferably acetone.

The resulting solution of crude pimecrolimus is further purified by HPLC. The feed solution is prepared by evaporating the solvent and adding a solvent mixture which is similar to the mobile phase, but contains enough components which are good solvents for pimecrolimus, preferably isopropanol, methyl-tert-butylether and n-heptane. If acetonitrile/water (e.g., 12% (w/w) water:88% (w/w) acetonitrile) is used as mobile phase, for example, the same solvent mixture (12% (w/w) water:88% (w/w) acetonitrile) can be used for preparation of the feed solution.

Figure 2:
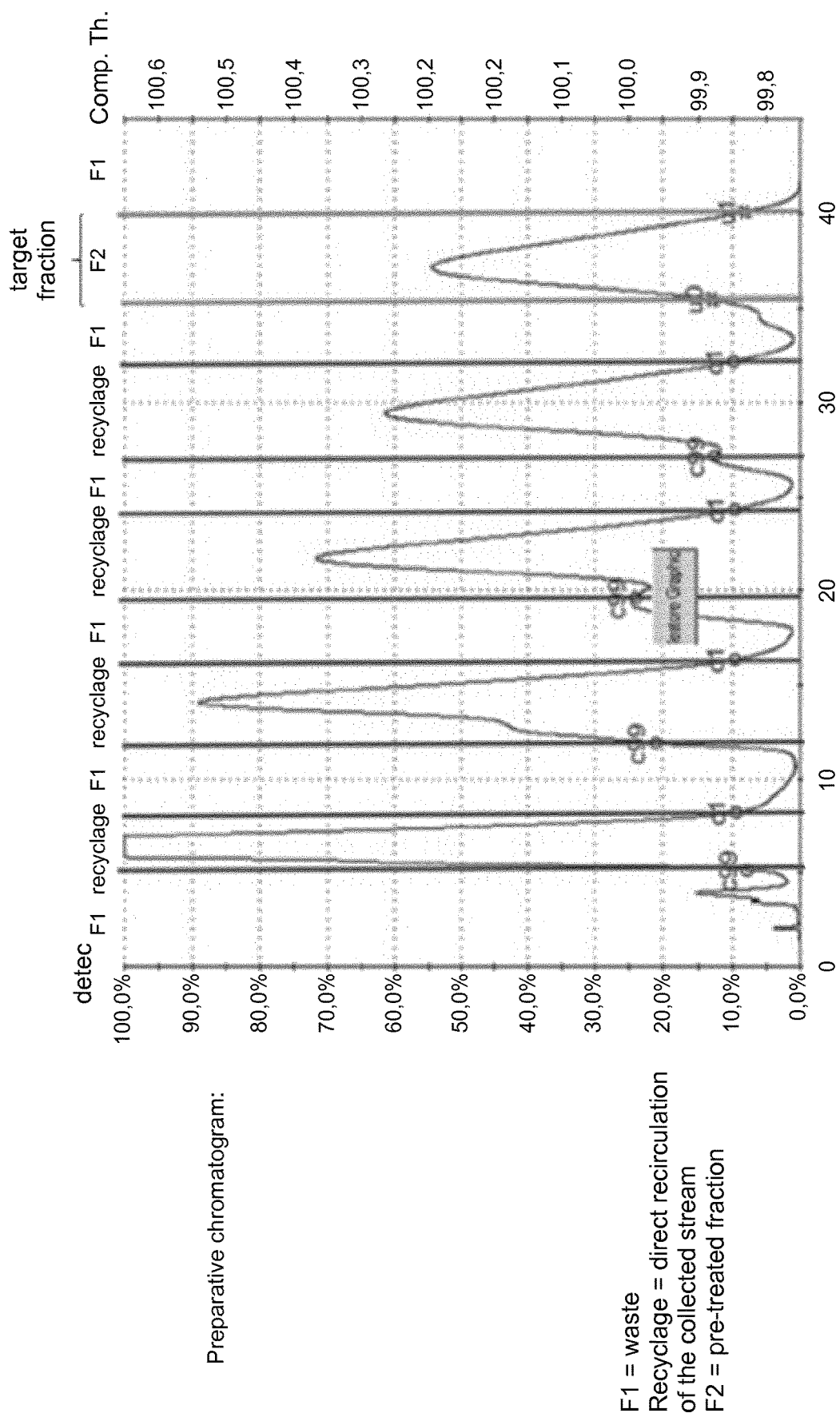
FIG. 2 shows an example of a preparative HPLC chromatogram obtained in Example 2.

Those of ordinary skill in the art will understand that purification of the crude pimecrolimus via high-pressure liquid chromatography will result in waste fractions and a main fraction containing pimecrolimus. In some embodiments, a main fraction obtained via high-pressure liquid chromatography may be further purified by high-pressure liquid chromatography by recirculating the main fraction to give a target fraction. In some embodiments, the waste fractions are removed from the main fraction and discarded. In some embodiments, the target fraction is obtained after three to six such recirculation cycles. In one embodiment, four recirculation cycles are preferred. In some embodiments, the main fraction is concentrated, dissolved in an appropriate solvent (e.g., a solvent mixture which is similar to the mobile phase, but contains enough components which are good solvents for pimecrolimus as described above) and recirculated. FIG. 2 shows an example of a chromatogram of a stream subjected to such recirculation; after a first HPLC cycle, fraction F1 is discarded, and the recycle fraction is further subjected to HPLC; this process is repeated until the target fraction F2 is obtained.

In one embodiment of the present disclosure, the HPLC purification is performed using a stationary phase including an alkylated silica stationary phase. The alkylated silica stationary phase may be a methyl-, butyl-, octyl-, dodecyl-, or octadecyl silca. The alkylated silica may be selected from commercially available alkylated silicas such as Daisogel C1-P, Daisogel C4-P, Daisogel C8-P, Daisogel ODS, Phenomenex Luna Prep C18(2), YMC Pack ODS-AQ 12S11, YMC ODS-AQ (10 μm, 120 Å), or Kromasil C18. Suitable mobile phases for use with such a stationary phase include water plus $C_1$-$C_3$ alcohols (e.g., methanol, ethanol, propanol, isopropanol) or acetonitrile, optionally further including an ether (for example, methyl-tert-butylether or diethylether), and/or optionally further including an acid, for example $H_3PO_4$ or TFA. Optimization of ether and/or acid concentrations in the mobile phase is within the knowledge of those of ordinary skill in the art.

In a preferred embodiment, the HPLC purification is performed using octadecyl-silica as stationary phase and as mobile phase water:methanol or water:acetonitrile. A concentration of acetonitrile of 84% (w/w) or higher is especially preferred, such as, e.g., 12% (w/w) water:88% (w/w) acetonitrile.

In order to increase productivity, the crude pimecrolimus can be pretreated by chromatography at higher loading over an octadecyl silica column. This treatment separates triphenylphosphine oxide, ascomycin and 33-epi-chloro-$\Delta^{23,24}$-ascomycin from pimecrolimus.

Preferred temperatures for the chromatography with methanol:water are from 35 to 70° C., preferably 45 to 55° C., more preferably 50° C.

In another embodiment of the invention the HPLC is performed using a diol-silica as stationary phase. The diol-silica may be any diol-silica, such as commercially available diol-silicas such as YMC Pack-120-HG, YMC Pack-80-HG, and Kromasil 60-10 Diol. Mobile phases may include a nonpolar solvent, e.g. alkanes, cycloalkanes, petrolether; plus a polar protic solvent, e.g. alcohols, water; plus optionally a polar aprotic solvent, e.g. ethers, preferably methyl-tert-butylether; cyclic ethers, preferably THF; esters, preferably ethyl acetate; halogenated solvents, preferably dichloromethane. Preferred mobile phases are $C_5$-$C_8$ alkanes (e.g., pentane, hexane, heptane, or octane) or cycloalkanes (such as cyclohexane, methylcyclohexane, dimethylcyclohexane), plus an ether such as methyl-tert.-butylether, tetrahydrofuran, plus isopropanol or ethanol. Optimization of solvent ratios in the mobile phase is within the knowledge of those of ordinary skill in the art.

In one embodiment, the HPLC is performed using Kromasil 60-10 Diol, 60 Å pore, 10 μm particles as stationary phase and heptane 81.1±0.5% (w/w):methyl-tert.-butylether 14.4±0.5% (w/w):isopropanol (IPA) 4.5 (4.2-4.9) % (w/w) as mobile phase; i.e., the isopropanol may be 4.2-4.9% (w/w) of the mobile phase, such as 4.5% (w/w).

In another embodiment, the HPLC is performed using a cyano-silica stationary phase. The cyano-silica may be any cyano-silica, such as commercially available cyano-silicas including Phenomenex Luna CN. Mobile phases in such an embodiment may include water+$C_1$-$C_3$ alcohols (methanol, ethanol, propanol, isopropanol). A preferred mobile phase is water+methanol (35% (w/w)+65% (w/w)). This chromatographic system is able to separate tautomeric forms of pimecrolimus.

The combined chromatographic main fractions are evaporated on a thin-layer evaporator in vacuum (at 150 mbar). The residue is dissolved in acetone. The side fractions are combined and further purified in a second chromatographic step.

The obtained pimecrolimus is further purified by crystallization from suitable solvents, for example ethyl acetate cyclohexane/water, acetone/heptane. Preferred solvents are ethanol/water with evaporation and drying steps. When using ethanol/water to crystallize, the substance is first subjected to solvent exchange (i.e., acetone to ethanol). Water is then added to the ethanol solution during crystallization, and seeding may also be used. The resulting product has a chromatographic purity of >99% (w/w).

By purifying the crude pimecrolimus product via HPLC, the need for expensive and extensive counter-current extractions (such as those disclosed in U.S. Pat. No. 7,148,346, which is incorporated herein by reference) is avoided. Thus, in one embodiment, the present invention includes a process for the preparation of pimecrolimus wherein the pimecrolimus is not subjected to further purification steps beyond HPLC and crystallization. This results in a commercial-scale process that can produce large quantities of purified pimecrolimus, including substantially pure pimecrolimus, in high yields and with less extensive workup.

FIG. 1 shows a flow chart comparing the process of the present disclosure to known processes. As discussed above, in preparation of the crude pimecrolimus, the process of the present invention carries out the chlorination reaction in a similar way but a counter current extraction of the starting material (ascomycin) is not required, while it is in known processes. In the preparation of the pimecrolimus active substance from the crude pimecrolimus (i.e., the purification step(s)), the "step 1" of known processes is not required; instead, HPLC chromatography is used, yielding purified pimecrolimus.

Example 1

Chlorination of crude ascomycin 121 kg (containing 116.9 kg 100%, ascomycin) commercially available ascomycin (assay >90%) is placed in a reactor, and toluene is added and distilled off in vacuum in order to dry the ascomycin azeotropically. The residue is dissolved in THF, which is again distilled off and substituted by fresh THF.

In a different reactor 40 kg triphenylphosphine are dissolved in THF. To this solution 21.3 kg N-chlorosuccinimide are added in portions. This reaction mixture is stirred at room temperature, then 40 L collidine is slowly added keeping the temperature at room temperature. The ascomycin solution in THF is pumped in and stirred for at 39° C. The batch is analyzed for ascomycin content. If ascomycin content is too high, further quantities of triphenylphosphine and NCS are added and stirring is continued.

The reaction mixture is cooled to 20° C. Cyclohexane is fed in, and a solution of 40 kg citric acid in water and methanol is added at 20° C. Phases are separated. The upper organic phase is washed with a mixture of water and methanol. Washing is repeated. Lower phases are combined and re-extracted with cyclohexane twice. Combined organic phases are washed with water. Then cyclohexane is evaporated. The thick residue is dissolved in acetone. Solvent is evaporated and residue is finally dissolved in 400 kg acetone. This solution contains 103 kg (86% of theory) pimecrolimus, having a chromatographic purity of >70%, not more than 10% (w/w) ascomycin, and not more than 20% (w/w) 33-epi-chloro-$\Delta^{23,24}$-ascomycin.

HPLC Purification 57.1 kg of this solution having an assay of 17.52% (w/w) pimecrolimus (=10 kg pimecrolimus) are evaporated to dryness, dissolved in a mixture of isopropanol, methyl-tert-butylether and n-heptane to get 181 kg feed solution and filtered over 1.5 kg silica gel. The filtered solution is used as a feed for chromatographic purification on a column filled with Kromasil 60-10 Diol, 60 Å pore, 10 μm particles as stationary phase. The mobile phase used is 81.1% (w/w) heptane, 14.4% (w/w) methyl-tert-butylether, 4.5% (w/w) isopropanol. When changing from feed solution to mobile phase, surprisingly no crystallization of pimecrolimus occurs, even though pimecrolimus is not soluble in this mixture at the feed concentration.

The separation is followed with UV detector at wavelength of 254 nm and the eluate is separated into empty, side and main fractions, based on the signal. When elution is complete, the column is regenerated with pure isopropanol, and conditioning is performed with mobile phase due to high $\Delta$ P in two portions.

The combined main fractions are evaporated on a thin-layer evaporator in vacuum (at 150 mbar). The residue is dissolved in acetone. 106.8 kg acetone solution with a pimecrolimus concentration of 6.5% (w/w) is obtained. This equals 6.94 kg pimecrolimus from 10 kg pimecrolimus in the crude feed solution resulting in a yield from the main fractions of 69% of theory.

The side fractions are concentrated in the same way as the main fractions. Another 54 kg acetone solution containing 4.6% (w/w) pimecrolimus is obtained, which are another 2.5 kg pimecrolimus, yield 25% of theory. This material is recycled into the chromatography step giving main fractions containing another 0.65 kg (26% of theory) pimecrolimus. The combined yield of pimecrolimus from main fractions is 7.59 kg (75.9% of theory).

Concentration and Crystallization:

The concentrate of the main fractions dissolved in acetone containing 111.2 kg pimecrolimus are combined in a vessel. The solution is filtered and concentrated in vacuum. Ethanol is added. Acetone and ethanol are distilled off in vacuum, while further ethanol is added to keep the concentration constant. Finally, the concentration is adjusted to 25% (w/w) pimecrolimus by addition of ethanol.

A suspension of pimecrolimus in a mixture of water and ethanol is prepared as a crystallization seed suspension.

The 25% (w/w) pimecrolimus solution in ethanol is heated to reflux temperature for 30 min, cooled to 55° C., and the seed suspension is added. The mixture is stirred for another (up to) 45 min at 55° C. Demineralized water is added within 2 h. The mixture is stirred for another 30 min at 55° C. The suspension is cooled to 10° C. and stirred at 10° C.

The crystals are filtered through a filter-dryer. The cake is washed 3 times with 33% (w/w) aqueous ethanol. The cake is dried in the filter-dryer at 48° C. jacket temperature in vacuum until water content is below 0.1% (w/w), yielding 105.6 kg pure pimecrolimus (95% of theory).

The overall yield calculated for commercial ascomycin is 86%×75.9%×95%=62%. The purified pimecrolimus prepared has an assay of 100.9% (w/w) and a chromatographic purity of 99.52% (w/w). This value represents 100% minus total impurities.

Example 2

Ascomycin was chlorinated to crude pimecrolimus as described in Example 1.

Chromatographic pre-treatment:

On a column 50 mm diameter×250 mm height filled with C18-silica stationary phase (Daiso), 7.4 g of crude pimecrolimus (assay 50.4% (w/w), containing 3.73 g 100% pure pimecrolimus) were injected as a solution in 12% (w/w) water/88% (w/w) acetonitrile. with a concentration of 200 g crude pimecrolimus/L (high load). Pimecrolimus was eluted with 12% (w/w) water 88% (w/w) acetonitrile. The target fractions contained 3.62 g (97% of the input) pimecrolimus in a chromatographic purity of 84% (w/w).

The solvent was evaporated from the target fractions and the residue was dissolved in a concentration of 70 g/l in the eluent 12% (w/w) water/88% (w/w) acetonitrile. This solution was injected in a column 50 mm diameter×250 mm height filled with C18-silica stationary phase (Daiso), and was subjected to chromatographic purification with recirculation. Eluent 12% (w/w) water:88% (w/w) acetonitrile, 4 recirculation cycles, as shown in FIG. 2.

The target fraction (as indicated in FIG. 2) contained 2.97 g (82% of input) of pimecrolimus in a purity of 98.43% (w/w). This corresponds to a productivity of 120 g crude pimecrolimus per kg of stationary phase per day.

The target fraction was concentrated and crystallized from ethanol/water as described in Example 1.

Example 3

Ascomycin was chlorinated to crude pimecrolimus as described in Example 1.

Chromatographic pre-treatment:

On a column 50 mm diameter×250 mm height filled with C18-silica stationary phase (Daiso), 7.8 g of crude pimecrolimus (assay 50.3% (w/w), containing 3.92 g of 100% pure pimecrolimus) were injected as a solution in 12% (w/w) water:88% (w/w) acetonitrile with a concentration of 200 g crude pimecrolimus/l. Pimecrolimus was eluted with 12% (w/w) water:88% (w/w) acetonitrile. The target fractions contained 3.77 g (96% of the input) pimecrolimus in a chromatographic purity of 81.3% (w/w).

The solvent was evaporated from the target fractions and the residue was dissolved in a concentration of 65 g/l in the eluent 12% (w/w) water:88% (w/w) acetonitrile. This solution was injected in a column 50 mm diameter×250 mm height filled with C18-silica stationary phase (Daiso), and was subjected to chromatographic purification with recirculation. Eluent 12% (w/w) water:88% (w/w) acetonitrile, 6 recirculation cycles.

The target fraction contained 2.83 g (75% of input) of pimecrolimus in a purity of 98.92% (w/w). This corresponds to a productivity of 200 g crude pimecrolimus/kg of stationary phase/day. The target fraction was evaporated to dryness.

The residue was dissolved in 3 parts of ethanol 94% (w/w) at 75° C. The solution was cooled to 55° C. before seeding: crystallization occurred; 1.5 parts of water were added slowly. The solution was cooled to 10° C. The mixture was aged overnight at 10° C. The product was filtrated, washed with 1 volume of cold water, and dried at 50° C. 2.72 g pimecrolimus (96% of input) was isolated.

The overall yield calculated on commercial ascomycin is 86%×96%×75%×96%=59.4%.

The pimecrolimus prepared has an assay of 100.07% (w/w) and a chromatographic purity of 99.71 area %.

Example 4

Ascomycin was chlorinated to crude pimecrolimus as described in Example 1.

Crude pimecrolimus (assay 62.8% (w/w)) was chromatographed on the stationary phase YMC ODS-AQ (10 µm, 120 Å). As mobile phase was used 70% (w/w) methanol+30% (w/w) water. The chromatography was run at 50° C. twice. The first run achieved a purity of the main fraction of 87 area %. The second run, using the main fraction of the first one as feed, achieved a purity of 97 area % in the main fraction and the yield of pimecrolimus in this fraction was 63.9%.

After crystallisation from ethanol water as described in the previous examples a chromatographic purity of 99.8 area % could be achieved.

Example 5 (Comparative Example)

In a comparative example using a crude ascomycin as starting material, pimecrolimus was prepared using the methods described in examples 3 and 4 of WO2006/040111. A solution of 1 g triphenylphosphine in 10 ml of tetrahydrofuran (THF) was added dropwise to 0.51 g NCS in 12 ml of THF. The resulting mixture was stirred 0.5 h at room temperature (22° C.). Then 1 ml pyridine was added followed by a solution of 2.45 g of dry technical ascomycin in 20 ml of THF. The resulting mixture was stirred for 1 h at 65° C. The mixture was diluted with toluene (45 ml), water was added (2×40 ml) and the resulting two phases were separated. The organic layer was washed with 1 N HCl (40 ml), water (40 ml), saturated aqueous sodium chloride solution (40 ml) and dried with sodium sulfate ($Na_2SO_4$). The solvent was evaporated from the resulting solution.

The residue was purified by chromatography on silica gel. 2.8 g of dry residue was dissolved in 6 ml of EtOAc, and 11 ml heptane was added dropwise resulting in 17.5 ml of solution (content of EtOAc=35 vol %). 16.5 ml of this feed solution was injected on a chromatography column with the following specifications:
L=45 cm
D=25 mm
V=220 ml
SF=Silicagel MB 40-75µ (prepared in mobile phase)
Mobile Phase:
heptane 6.5 L
EtOAc 2.5 L
~28 vol % EtOAc
Injection: 16.5 ml
Temperature: ambient Fractions F3 to F8 containing pimecrolimus were pooled together and after evaporation the dry residue weighed 0.9 g.

In 100 mL glass reactor dry residue (0.9 g) from chromatography was dissolved in 6.0 mL of ethanol and 2.2 mL demineralized water was added. Mixture was stirred at 4° C. In 5 minutes, 0.6 mL demineralized water was added and stirred for another 30 minutes. Then it was cooled to 0° C. After 3 hours of stirring mixture was turbid but product did not crystallize. 5 mL of water was added and stirred at 0° C. for another 22 hours. The suspension was filtered and crystals were dried at 40° C. and 100 mbar. 0.6 g crystalline pimecrolimus was obtained and analyzed. The analysis gave the following composition:

| Compound | Assay | Specification |
|---|---|---|
| pimecrolimus | 93.34% | >99.1% |
| C21 desmethylene pimecrolimus | 0.59% | <0.40% |
| C19 ethyl-pimecrolimus + C11 ethyl-pimecrolimus | 1.47% | ≤0.10% |
| C17 ethyl-pimecrolimus | 0.50% | ≤0.30% |
| $\Delta^{33,\,34}$ olefin | 3.02% | ≤0.30% |
| C21 epimer of pimecrolimus | 0.56% | ≤0.10% |
| 33-epi-chloro-$\Delta^{23,\,24}$-ascomycin | 0.38% | ≤0.15% |
| other related substance | 0.08% | ≤0.10% |
| total other related substances | 0.14% | ≤0.20% |
| total related substances | 6.66% | ≤0.90% |

As can be seen, the isolated pimecrolimus is not pure enough to be used as pharmaceutical active ingredient as it does not meet the required specifications for purity and potency.

All reagents and solvents described herein are suitably of the purity or grade specified, or otherwise of reagent grade or analytical grade, or of up to the highest purity available commercially or by methods known to persons of ordinary skill in the art.

While the aspects described herein have been described in conjunction with the example aspects outlined above, various alternatives, modifications, variations, improvements, and/or substantial equivalents, whether known or that are or may be presently unforeseen, may become apparent to those having at least ordinary skill in the art. Accordingly, the example aspects, as set forth above, are intended to be illustrative, not limiting. Various changes may be made without departing from the spirit and scope of the disclosure. Therefore, the disclosure is intended to embrace all known or later-developed alternatives, modifications, variations, improvements, and/or substantial equivalents.

Reference to an element in the singular is not intended to mean "one and only one" unless specifically so stated, but rather "one or more." All structural and functional equivalents to the elements of the various aspects described throughout this disclosure that are known or later come to be known to those of ordinary skill in the art are expressly incorporated herein by reference. Moreover, nothing disclosed herein is intended to be dedicated to the public.

Further, the word "example" is used herein to mean "serving as an example, instance, or illustration." Any aspect described herein as "example" is not necessarily to be construed as preferred or advantageous over other aspects. Unless specifically stated otherwise, the term "some" refers to one or more. Combinations such as "at least one of A, B, or C," "at least one of A, B, and C," and "A, B, C, or any combination thereof" include any combination of A, B, and/or C, and may include multiples of A, multiples of B, or multiples of C. Specifically, combinations such as "at least one of A, B, or C," "at least one of A, B, and C," and "A, B, C, or any combination thereof" may be A only, B only, C only, A and B, A and C, B and C, or A and B and C, where any such combinations may contain one or more member or members of A, B, or C.

Moreover, all references throughout this application, for example patent documents including issued or granted patents or equivalents; patent application publications; and non-patent literature documents or other source material; are hereby incorporated by reference herein in their entireties, as though individually incorporated by reference.

What is claimed is:

1. A process for preparing purified pimecrolimus, comprising:
  a) chlorinating crude ascomycin to provide crude pimecrolimus;
  b) purifying the crude pimecrolimus by high-pressure liquid chromatography to provide purified pimecrolimus,
  wherein the crude ascomycin comprises more than 0.2% (w/w) 21-desmethylene ascomycin, more than 0.1% (w/w) 17-ethylascomycin, more than 0.1% (w/w) 21-epi-ascomycin and 11-ethylascomycin and not more than 96% (w/w) ascomycin.

2. The process of claim 1, wherein said chlorinating step comprises chlorinating the crude ascomycin with dichlorotriphenylphosphorane in an organic solvent.

3. The process of claim 2, wherein said chlorinating step comprises generating a chlorinating agent in situ from reaction of triphenylphosphine with a chlorinated alkane or N-chlorosuccinimide.

4. The process of claim 3, wherein said chlorinating agent is dichlorotriphenylphosphorane.

5. The process of claim 1, wherein the crude ascomycin contains not less than 90% ascomycin.

6. The process of claim 1, wherein the crude ascomycin contains up to 2% (w/w) 21-desmethylene ascomycin, up to 1.5% (w/w) 17-ethylascomycin, and/or up to 4% (w/w) 21-epi-ascomycin and 11-ethylascomycin.

7. The process of claim 1, wherein the crude ascomycin is a technical-grade ascomycin.

8. The process of claim 1, wherein the crude ascomycin is not purified prior to the chlorinating step.

9. The process of claim 1, wherein said purified pimecrolimus contains a reduced concentration of the C21 epimer of pimecrolimus or one or more of the homologues of pimecrolimus, which differ only by 1 methylene group present at position C19, C17, C11 or absent at position C21, relative to the crude pimecrolimus.

10. The process of claim 1, wherein purifying the crude pimecrolimus via high-pressure liquid chromatography generates a target fraction containing pimecrolimus, and further comprising the step of crystallizing the pimecrolimus in said target fraction to provide purified pimecrolimus.

11. The process of claim 10, wherein purifying the crude pimecrolimus via high-pressure liquid chromatography comprises the steps of:
   i) purifying crude pimecrolimus via high-pressure liquid chromatography to give a main fraction, wherein said main fraction contains pimecrolimus;
   ii) concentrating and then diluting the main fraction;
   iii) recirculating the main fraction through high-pressure liquid chromatography; and
   iv) optionally repeating steps ii) and iii),
   to generate the target fraction containing pimecrolimus.

12. The process of claim 1, wherein the crude pimecrolimus is not subjected to further purification steps.

13. The process of claim 1, wherein the high-pressure liquid chromatography uses a stationary phase selected from the group consisting of an alkylated silica, a diol silica, or a cyano silica.

14. The process of claim 1, wherein the high-pressure liquid chromatography uses a mobile phase selected from the group consisting of:
   a nonpolar solvent, polar protic solvent, and optional polar aprotic solvent;
   one or more $C_5$-$C_8$ alkanes, an ether, and isopropanol;
   one or more $C_5$-$C_8$ cycloalkanes, an ether, and isopropanol;
   one or more $C_5$-$C_8$ alkanes, an ether, and ethanol;
   one or more $C_5$-$C_8$ cycloalkanes, an ether, and ethanol;
   heptane 81.1±0.5% : methyl-tert-butylether 14.4±0.5% : isopropanol 4.5 (4.2-4.9) %;
   $C_1$-$C_3$ alcohols or acetonitrile, optionally an ether, and optionally an acid; or
   water, a water miscible solvent, optionally an ether, and optionally an acid.

15. The process of claim 1, wherein step b) comprises purifying the crude pimecrolimus by high-pressure liquid chromatography over an octadecyl silica stationary phase with a 30% water : 70% methanol mobile phase.

16. The process of claim 1, wherein the purified pimecrolimus has a chromatographic purity of more than 98% pure.

17. The process of claim 1, wherein the purified pimecrolimus has a chromatographic purity of more than 99% (w/w).

18. The process of claim 1, wherein the purified pimecrolimus has a chromatographic purity of more than 99.5% (w/w).

19. A process for preparing purified pimecrolimus, the process comprising:
   a) purifying a crude pimecrolimus via high-pressure liquid chromatography to generate a target fraction containing pimecrolimus, wherein said crude pimecrolimus is prepared by chlorination of crude ascomycin without further purification of the crude ascomycin;
   b) crystallizing the pimecrolimus in the target fraction to give purified pimecrolimus,
   wherein the crude ascomycin comprises more than 0.2% (w/w) 21-desmethylene ascomycin, more than 0.1% (w/w) 17-ethylascomycin, more than 0.1% (w/w) 21-epi-ascomycin and 11-ethylascomycin and not more than 96% (w/w) ascomycin.

20. The process of claim 19, wherein the purified pimecrolimus has a chromatographic purity of more than 99% (w/w).

21. The process of claim 19, wherein the purified pimecrolimus has a chromatographic purity of more than 99.5% (w/w).

22. The process of claim 19, wherein the crude ascomycin contains not less than 90% ascomycin.

23. The process of claim 19, wherein the crude ascomycin contains up to 2% (w/w) 21-desmethylene ascomycin, up to 1.5% (w/w) 17-ethylascomycin, and/or up to 4% (w/w) 21-epi-ascomycin and 11-ethylascomycin.

24. The process of claim 19, wherein the crude ascomycin is a technical-grade ascomycin.

25. A process for preparing purified pimecrolimus, the process consisting essentially of:
   a) chlorinating crude ascomycin to give crude pimecrolimus;
   b) purifying the crude pimecrolimus via high-pressure liquid chromatography to generate a target fraction containing pimecrolimus; and
   c) crystallizing the pimecrolimus in the target fraction to give purified pimecrolimus,
   wherein the crude ascomycin comprises more than 0.2% (w/w) 21-desmethylene ascomycin, more than 0.1% (w/w) 17-ethylascomycin, more than 0.1% (w/w) 21-epi-ascomycin and 11-ethylascomycin and not more than 96% (w/w) ascomycin.

26. The process of claim 25, wherein step b) includes:
   i) purifying crude pimecrolimus via high-pressure liquid chromatography to give a main fraction, wherein said main fraction contains pimecrolimus;
   ii) concentrating and then diluting the main fraction;
   iii) recirculating the main fraction through high-pressure liquid chromatography; and
   iv) optionally repeating steps ii) and iii),
   to generate the target fraction containing pimecrolimus.

27. The process of claim 25, the process consisting of:
   a) chlorinating crude ascomycin to give crude pimecrolimus;
   b) purifying the crude pimecrolimus via high-pressure liquid chromatography to generate a target fraction containing pimecrolimus; and
   c) crystallizing the pimecrolimus in the target fraction to give the purified pimecrolimus.

* * * * *